(12) United States Patent
Golden et al.

(10) Patent No.: US 7,951,165 B2
(45) Date of Patent: May 31, 2011

(54) ENDOSCOPIC MEDICAL INSTRUMENT AND RELATED METHODS OF USE

(75) Inventors: John Golden, Norton, MA (US); Liem T. Vu, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 913 days.

(21) Appl. No.: 10/642,152

(22) Filed: Aug. 18, 2003

(65) Prior Publication Data

US 2005/0043758 A1  Feb. 24, 2005

(51) Int. Cl.
*A61B 17/29* (2006.01)

(52) U.S. Cl. ....................................................... 606/205

(58) Field of Classification Search .................. 606/205, 606/207, 208; 600/562, 564
See application file for complete search history.

(56) References Cited

U.S. PATENT DOCUMENTS

| | | | |
|---|---|---|---|
| 4,763,669 A * | 8/1988 | Jaeger | 600/564 |
| 4,953,559 A | 9/1990 | Salerno | |
| 5,133,727 A | 7/1992 | Bales et al. | |
| 5,295,990 A | 3/1994 | Levin | |
| 5,374,277 A * | 12/1994 | Hassler | 606/207 |
| 5,396,900 A | 3/1995 | Slater et al. | |
| 5,419,339 A | 5/1995 | Palmer | |
| 5,439,478 A * | 8/1995 | Palmer | 606/205 |
| 5,454,378 A | 10/1995 | Palmer et al. | |
| 5,462,546 A | 10/1995 | Rydell | |
| 5,476,099 A * | 12/1995 | Robinson et al. | 600/564 |
| 5,482,054 A | 1/1996 | Slater et al. | |
| 5,558,100 A | 9/1996 | Cox | |
| 5,601,599 A | 2/1997 | Nunez | |
| 5,603,711 A | 2/1997 | Parins et al. | |
| 5,683,388 A | 11/1997 | Slater | |
| 5,706,824 A | 1/1998 | Whittier | |
| 5,722,421 A | 3/1998 | Francese et al. | |
| 5,743,906 A | 4/1998 | Parins et al. | |
| 5,819,738 A | 10/1998 | Slater | |
| 5,928,163 A | 7/1999 | Roberts et al. | |
| 5,976,130 A | 11/1999 | McBrayer et al. | |
| 6,036,656 A | 3/2000 | Slater | |
| 6,053,933 A | 4/2000 | Balazs et al. | |
| RE36,795 E | 7/2000 | Rydell | |

(Continued)

FOREIGN PATENT DOCUMENTS

DE  10004869 A  8/2000

(Continued)

OTHER PUBLICATIONS

Patent Abstracts of Japan, vol. 2000, No. 13, Feb. 5, 2001, Japan.

(Continued)

*Primary Examiner* — (Jackie) Tan-Uyen T Ho
*Assistant Examiner* — Ryan J Severson
(74) *Attorney, Agent, or Firm* — Finnegan, Henderson, Farabow, Garrett & Dunner, LLP (57) ABSTRACT

A medical instrument has a tubular member having a distal end and a proximal end, a handle attached to the proximal end of the tubular member, a distal assembly including a pivot and an end effector assembly supported on the pivot. The end effector assembly has a pair of end effectors. The medical instrument also includes an elongate member corresponding to each of the pair of end effectors. Each elongate member extends through the tubular member and has a proximal end attached to the handle and a distal end attached to the end effector assembly.

47 Claims, 10 Drawing Sheets

U.S. PATENT DOCUMENTS

| | | | |
|---|---|---|---|
| 6,152,924 A | 11/2000 | Parins | |
| 6,261,242 B1 | 7/2001 | Roberts et al. | |
| 6,440,085 B1 | 8/2002 | Krzyzanowski | |
| 6,458,130 B1 * | 10/2002 | Frazier et al. | 606/51 |
| 6,554,850 B1 * | 4/2003 | Ouchi et al. | 606/205 |
| 6,582,451 B1 | 6/2003 | Marucci et al. | |
| 6,616,662 B2 | 9/2003 | Scholer et al. | |
| 6,689,122 B2 | 2/2004 | Yamamoto | |
| 6,692,445 B2 | 2/2004 | Roberts et al. | |
| 6,767,349 B2 | 7/2004 | Ouchi | |
| 6,951,560 B1 | 10/2005 | Kidooka | |
| 6,969,389 B2 | 11/2005 | Kidooka | |
| 7,033,315 B2 | 4/2006 | Smith | |
| 7,037,276 B2 | 5/2006 | Sayet et al. | |
| 7,052,489 B2 | 5/2006 | Griego et al. | |
| 7,105,000 B2 | 9/2006 | McBrayer | |
| RE39,415 E | 11/2006 | Bales et al. | |
| 7,171,839 B2 | 2/2007 | Krzyzanowski | |
| 7,186,261 B2 | 3/2007 | Prestel | |
| 7,311,674 B2 | 12/2007 | Gingrich et al. | |
| 7,326,209 B2 | 2/2008 | Kidooka | |
| 7,341,564 B2 | 3/2008 | Zwiefel et al. | |
| 7,354,439 B2 | 4/2008 | Kidooka | |
| 7,422,592 B2 | 9/2008 | Morley et al. | |
| 7,534,253 B2 | 5/2009 | Endara et al. | |
| 7,621,910 B2 | 11/2009 | Sugi | |
| 7,736,363 B2 | 6/2010 | Watnabe | |
| 7,749,222 B2 | 7/2010 | Lu et al. | |
| 7,775,989 B2 | 8/2010 | Nakao | |
| 2002/0143358 A1 * | 10/2002 | Domingo et al. | 606/190 |
| 2005/0240218 A1 | 10/2005 | Freed et al. | |
| 2006/0025780 A1 | 2/2006 | James | |
| 2006/0149222 A1 | 7/2006 | Okada | |
| 2006/0184198 A1 | 8/2006 | Bales et al. | |
| 2006/0206145 A1 | 9/2006 | Griego et al. | |
| 2007/0055172 A1 | 3/2007 | Ratnakar | |
| 2007/0078458 A1 | 4/2007 | Dumbauld et al. | |
| 2007/0149971 A1 | 6/2007 | Nishimura | |
| 2007/0198011 A1 | 8/2007 | Sugita | |
| 2007/0244507 A1 | 10/2007 | Szweda et al. | |
| 2007/0244508 A1 | 10/2007 | Weizman et al. | |
| 2007/0244509 A1 | 10/2007 | Weizman et al. | |
| 2007/0244510 A1 | 10/2007 | Weizman et al. | |
| 2007/0244511 A1 | 10/2007 | Weizman et al. | |
| 2007/0244512 A1 | 10/2007 | Measamer | |
| 2007/0244513 A1 | 10/2007 | Weizman et al. | |
| 2007/0244514 A1 | 10/2007 | Weizman et al. | |
| 2008/0064982 A1 | 3/2008 | Nowlin et al. | |
| 2008/0125769 A1 | 5/2008 | Suzuki et al. | |
| 2008/0171908 A1 | 7/2008 | Okada et al. | |
| 2008/0194910 A1 | 8/2008 | Miyamoto et al. | |
| 2009/0088738 A1 | 4/2009 | Guerra et al. | |
| 2009/0088739 A1 | 4/2009 | Hushka et al. | |
| 2009/0088740 A1 | 4/2009 | Guerra et al. | |
| 2009/0088741 A1 | 4/2009 | Hushka et al. | |
| 2009/0088744 A1 | 4/2009 | Townsend | |
| 2009/0088745 A1 | 4/2009 | Hushka et al. | |
| 2009/0088746 A1 | 4/2009 | Hushka et al. | |
| 2009/0088747 A1 | 4/2009 | Hushka et al. | |
| 2009/0131932 A1 | 5/2009 | Vakharia et al. | |
| 2009/0131933 A1 | 5/2009 | Ghabrial et al. | |
| 2009/0216078 A1 | 8/2009 | Iwanaga et al. | |
| 2009/0264918 A1 | 10/2009 | Endara et al. | |
| 2009/0287112 A1 | 11/2009 | Freeman | |
| 2010/0106068 A1 | 4/2010 | Karpiel et al. | |

FOREIGN PATENT DOCUMENTS

| | | |
|---|---|---|
| DE | 10043163 A | 6/2001 |
| EP | 317 526 | 5/1989 |
| EP | 1 371 322 A | 12/2003 |
| EP | 1 872 730 | 1/2008 |
| EP | 1 875 872 | 1/2008 |
| JP | 2-1251 | 1/1990 |
| JP | 06-296619 | 10/1994 |
| JP | 10-179602 | 7/1998 |
| JP | 11-19086 | 1/1999 |
| JP | 11-19087 | 1/1999 |
| JP | 11-155877 | 6/1999 |
| JP | 11-178829 | 7/1999 |
| JP | 11-216146 | 8/1999 |
| JP | 11-216148 | 8/1999 |
| JP | 2000-189431 | 7/2000 |
| JP | 2000-271128 | 10/2000 |
| JP | 2000 279418 A | 10/2000 |
| JP | 2000-296131 | 10/2000 |
| JP | 2001-112766 | 4/2001 |
| JP | 2003-93393 | 4/2003 |
| JP | 2003-126103 | 5/2003 |
| JP | 2003-299669 | 10/2003 |
| JP | 2003-310635 | 11/2003 |
| JP | 2004-97615 | 4/2004 |
| JP | 2004-229976 | 8/2004 |
| JP | 2005-058344 | 3/2005 |
| JP | 2005-193061 | 7/2005 |
| JP | 2005-237431 | 9/2005 |
| JP | 2006-296578 | 11/2006 |
| JP | 2006-296781 | 11/2006 |
| JP | 2006-334267 | 12/2006 |
| JP | 2006-334348 | 12/2006 |
| JP | 2007-260248 | 10/2007 |
| JP | 2007-330436 | 12/2007 |
| JP | 2009-153535 | 7/2009 |
| JP | 2009-297503 | 12/2009 |
| WO | WO 93/20754 | 10/1993 |
| WO | WO 94/17741 | 8/1994 |
| WO | WO 97/11643 | 4/1997 |
| WO | WO 03/028557 A | 4/2003 |
| WO | WO 2006/114952 | 11/2006 |
| WO | WO 2006/114989 | 11/2006 |

OTHER PUBLICATIONS

PCT Search Report dated Dec. 15, 2004.
PCT Written Opinion dated Dec. 15, 2004.

* cited by examiner

ENDOSCOPIC MEDICAL INSTRUMENT AND RELATED METHODS OF USE

FIELD OF THE INVENTION

The present invention relates to a medical instrument. More particularly, this invention relates to a medical instrument for performing an operation within a body cavity in conjunction with an endoscope, and, even more particularly, to an actuation mechanism for operating an end effector assembly of such an instrument.

BACKGROUND OF THE INVENTION

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member for insertion into a lumen of an endoscope. The tubular member is sufficiently long and flexible to follow a long, winding path of the body cavity. An end effector assembly, such as a biopsy forceps assembly, is attached at a distal end of the tubular member, and a handle is attached at a proximal end of the tubular member. An elongate mechanism, such as a pull wire, extends through the tubular member to connect the end effector assembly and the handle. A biopsy forceps assembly, for example, may include mating jaws actuated by the handle to sample a body tissue.

There are numerous types of endoscopic medical intruments in use today. These instruments have various actuator/end effector assemblies and connections configured to provide certain benefits. For example, one type of endoscopic medical instrument includes a single, elongate flexible pull wire extending through the instrument and connected at its distal end to a relatively rigid actuator having an axis along the instrument. That actuator includes a pair of pins at one end, each pin supporting an end of one link. The other end of each link connects to a jaw. A support pin supports the jaw assembly. This assembly can generate a relatively large closing force at the jaw assembly. The jaws of the jaw assembly pivot together about the support pin because they are connected to a single actuator. This limits the range of rotation of the jaws.

Another type of endoscopic medical instrument includes a pair of elongate, flexible pull wires extending through the instrument. Each wire connects at its distal end directly to a lever arm of a jaw. In this configuration, each jaw is supported on and pivots about a single pivot pin. With this assembly, as the wires are pulled proximally to close the jaws, the torque about the pivot pin decreases, thereby decreasing the closing force.

A further endoscopic medical instrument includes a jaw assembly with a pair of jaws connected to a pair of arms extending from a jaw housing. Each jaw has a shank that has a surface facing a surface on corresponding arms. A cam slot on each jaw shank is slidably engaged by a cam pin on the arms. A puller member axially movable within the housing supports a pair of pivots, each of which pivotally engages a jaw shank. The puller member is attached to a drive wire coaxially positioned in a tubular shaft such that axial movement of the drive wire actuates the puller member. In response to axial movement of the puller, the cam pins riding in the cam guide slots change the position relative to the fixed jaw pivot axis of the jaw, thus actuating the jaws.

Another endoscopic medical instrument includes a single flexible pull wire that connects at its distal end to a relatively short rigid tube. The tube extends over and moves axially relative to the jaw assembly to close the jaws.

SUMMARY OF THE INVENTION

In accordance with an aspect of the present invention, a medical instrument comprises a tubular member having a distal end and a proximal end, a handle attached to the proximal end of the tubular member, a pair of end effectors supported on a pivot, a link corresponding to each of the pair of end effectors, and an elongate member corresponding to each of the pair of end effectors. Each elongate member may extend through the tubular member and has a proximal end attached to the handle. A distal end of each link is connected to a corresponding end effector and a proximal end of each link is connected to a distal end of a corresponding elongate member.

According to another aspect of the invention, the medical instrument comprises a tubular member having a distal end and a proximal end, a handle attached to the proximal end of the tubular member, a distal assembly including a pivot and an end effector assembly supported on the pivot. The end effector assembly has a pair of end effectors. The distal assembly has a center axis and a pair of stops, each stop configured to prevent rotation of a corresponding end effector past the center axis. The medical instrument also includes an elongate member corresponding to each of the pair of end effectors. Each elongate member extends through the tubular member and has a proximal end attached to the handle and a distal end attached to the end effector assembly in a manner permitting positioning of one of the end effectors at a first angle relative to the center axis when the other of the end effectors is positioned at a second angle relative to the center axis that is different than the first angle.

In another aspect of the present invention, each of the elongate members may include a flexible wire. In a further aspect, each of the elongate members may include an actuator that has a proximal end connected to a distal end of the corresponding flexible wire and a distal end connected to a corresponding link. Each actuator may be more rigid than the corresponding flexible wire and may have a cross-section selected from one of semi-circular, circular, rectangular, and square.

In a further aspect, proximal displacement of the elongate member may cause a corresponding end effector to close while distal displacement of the elongate member may cause the corresponding end effector to open.

In still another aspect, each elongate member may be configured to move independently of the other elongate member.

In another aspect, the present invention may include a clevis attached to the distal end of the tubular member. The clevis may support a pivot pin that supports the end effectors. The clevis may have a center axis and each elongate member may extend substantially parallel to the center axis. In addition to the center axis, the clevis may also include a pair of stops where each stop is configured to prevent rotation of a corresponding end effector past the center axis. The clevis may have a main portion that has a through hole configured to receive the elongate members. The through hole may include two through holes, each being configured to receive one of the elongate members.

In a further aspect, each end effector may be a forceps jaw. One of the forceps jaws may have a planar distal portion and the other of the forceps jaws may have a cup-shaped distal portion. In a further aspect, regardless of the shape of the distal portions, at least one of the forceps jaws may include a cutting edge.

In yet another aspect, each end effector may include a first stop surface and a second stop surface. In a further aspect, the first stop surface of one of the end effectors may contact the second stop surface of the other of the end effectors to provide a maximum opening of the end effectors. In this arrangement, each elongate member may be configured to move independent of the other elongate member to allow the end effectors to rotate about the pivot when the end effectors are at the maximum opening.

In another aspect, at least the distal end of one elongate member may be displaceable a first amount proximally and at least the distal end of the other elongate member may be displaceable a second amount distally to allow the end effectors to rotate about the pivot. In addition, the first amount of displacement may be different than the second amount of displacement. This may allow the end effectors to rotate through different angles about the pivot.

According to other aspects, the present invention is directed to a method of performing a medical procedure. The method includes providing a medical instrument as set forth above, inserting the distal end of the tubular member and the pair of end effectors into a patient to a target site, manipulating the handle such that the elongate members are displaced to open the pair of end effectors, positioning the end effectors towards the target site, and manipulating the handle such that the elongate members are displaced to close the pair of end effectors on the target site to perform an operation. The term "providing" is used in a broad sense, and refers to, but is not limited to, making available for use, enabling useage, giving, supplying, obtaining, getting a hold of, acquiring, purchasing, selling, distributing, possessing, making ready for use, and/or placing in a position ready for use.

In another aspect, positioning the end effectors toward the target site may include contacting a tissue wall with one of the end effectors located proximally of the target site and displacing the tubular member to cause the end effectors to rotate towards the target site. Positioning the end effectors toward the target site may include contacting a tissue wall with one of the end effectors located distally of the target site and displacing the tubular member to cause the end effectors to rotate towards the target site.

In a further aspect, displacing the tubular member may cause the other end effector to contact one of the pair of stops of the distal assembly and prevent rotation of the other end effector past the center axis.

In another aspect, each end effector may include a first stop surface and a second stop surface, and displacing the tubular member may cause the first stop surface of one end effector to contact the second stop surface of the other end effector to provide a maximum opening of the end effectors.

In still another aspect, the end effectors may be forceps jaws and the operation may be to obtain a biopsy.

Additional aspects and advantages of the invention will be set forth in part in the description which follows, and in part will be obvious from the description, or may be learned by practice of the invention. The various aspects and advantages of the invention will be realized and attained by means of the elements and combinations particularly pointed out in the appended claims. The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

The various parts of the endoscopic medical instrument described herein may be made from any suitable biocompatible material known in the art.

The present invention relates to a medical instrument for, for example, use in conjunction with an endoscope for performing an operation within a body cavity of a patient. According to embodiments of the invention, the medical instrument generally includes an elongate, flexible tubular member having a distal end and a proximal end. A handle is attached to the proximal end of the tubular member. An end effector assembly, such as, for example, a biopsy forceps assembly, is attached to the distal end of the tubular member. A pair of elongate members, such as pull wires, connect at their proximal end to the handle, extend through the tubular member, and connect to end effectors at the distal end. In certain embodiments, the end effectors may be jaws of a jaw assembly.

According to embodiments of the invention, the medical instrument includes an actuator means for opening and closing the end effectors. The embodiments of the actuator mechanism provide a relatively large closing force, allow the end effector assembly to pivot more freely, and permit increased flexibility and ease of manipulation of the end effectors in situ without detraction of the closing force.

One exemplary actuator means includes a pair of actuators, each of which is connected at its distal end to an end effector via a link. Each proximal end of an actuator connects to a corresponding one of the pair of pull wires. This assembly permits each of the end effectors to pivot freely about a single pivot point while retaining a relatively large clamping force.

A further embodiment of actuation means includes passing the pair of pull wires through a distal clevis in separate holes extending through the clevis. Each of the pull wires connects at its proximal end to a handle and at its distal end to one of the end effectors. The geometry of the through holes in the clevis can be controlled so that the pull wires are constrained to move at an angle with respect to a centerline of the endoscopic medical instrument to provide for more torque and to increase the closing force.

Another embodiment of the actuation means includes a collar that is attached to the pull wires. The geometry of the collar is configured to interact with the clevis to generate an inwardly bending of the distal ends of the pull wires. This inwardly bending will also increase the amount of closing force generated.

Embodiments of the present invention will be shown and described in connection with biopsy forceps devices and forceps assemblies having a pair of jaws as end effectors. However, the actuation mechanisms are suitable for other types of endoscopic, laparoscopic, or other instruments and other types of end effector assemblies and end effectors, such as graspers, cutters, clampers, or other devices known in the art. The biopsy forceps devices shown and described are exemplary only.

Figure 1:
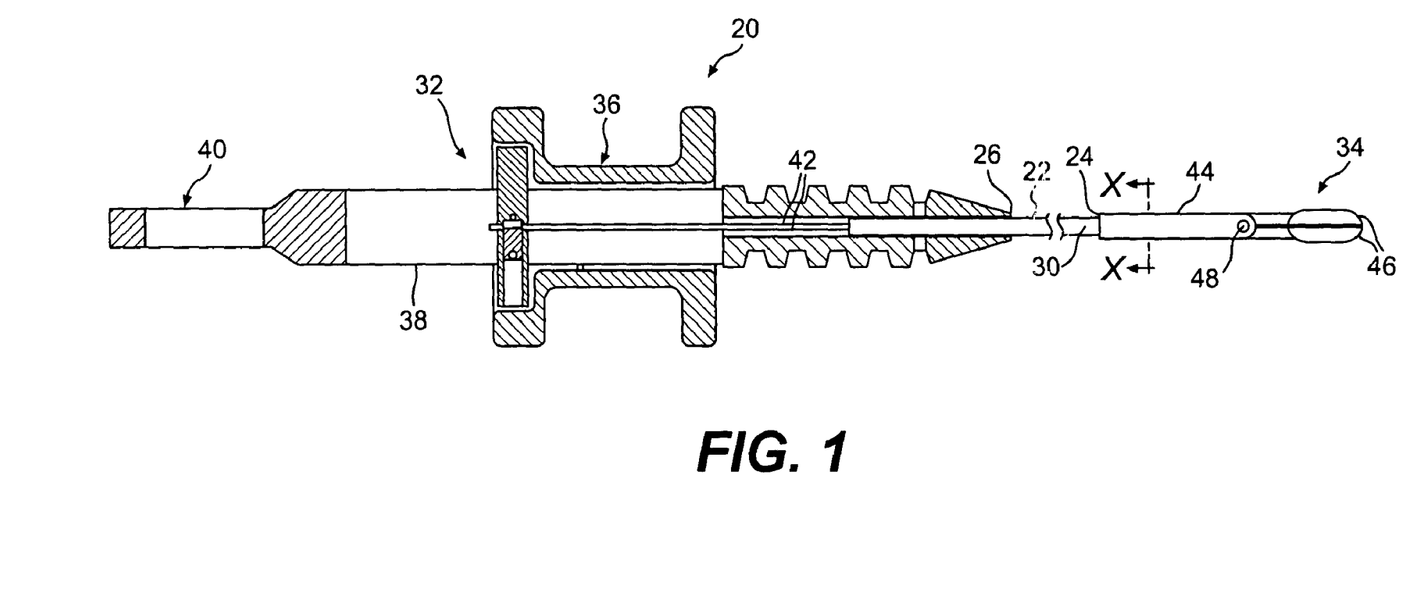
FIG. 1 is a side and partially cross-sectional view of an embodiment of an endoscopic medical instrument of the present invention.

In an embodiment of the present invention shown in FIG. 1, a biopsy forceps device 20 has a flexible tubular member 22 having a distal end 24 and a proximal end 26. During an operation on a patient to obtain a biopsy, distal end 24 travels through a lumen of an endoscope and the patient's body cavity. Proximal end 26 of tubular member 22 remains outside the body cavity.

Figure 2:
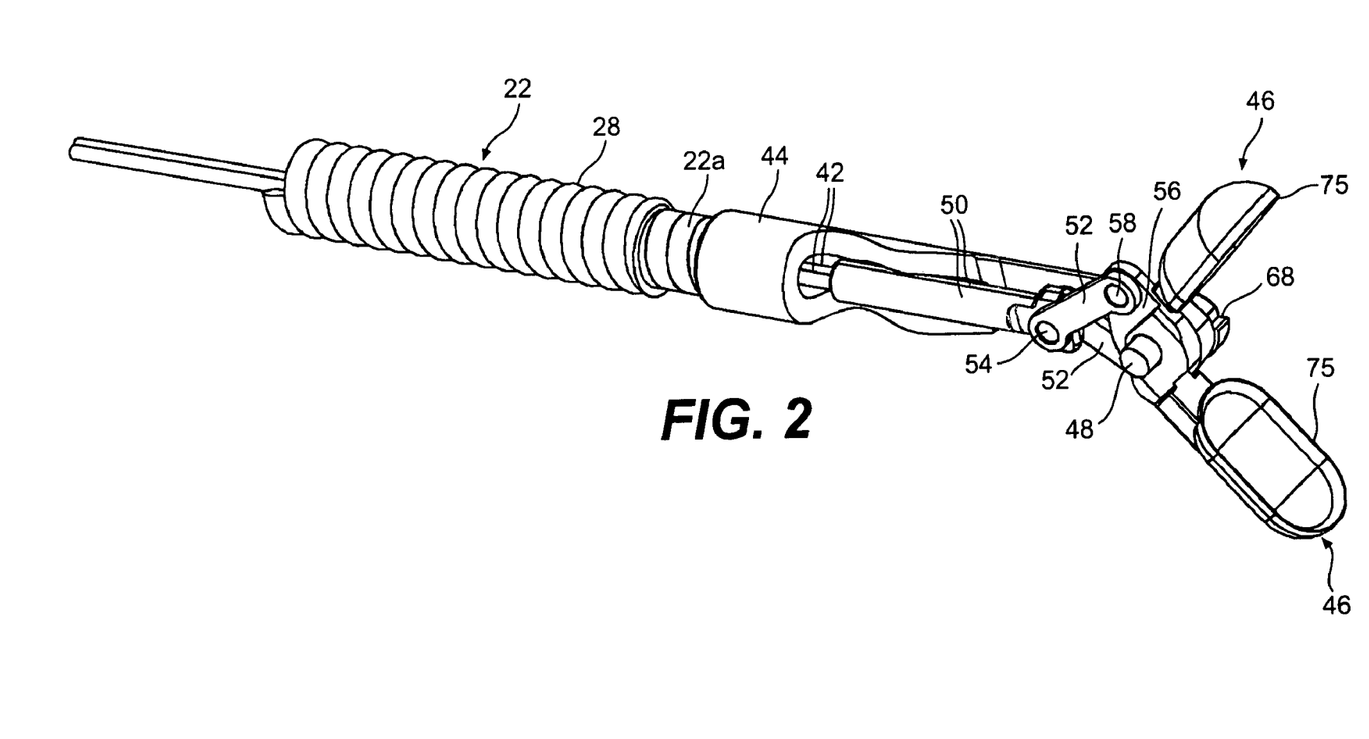
FIG. 2 is a perspective view of the distal end of the endoscopic medical instrument shown in FIG. 1 with an outer sheath and portions of the clevis removed.
Figure 3:
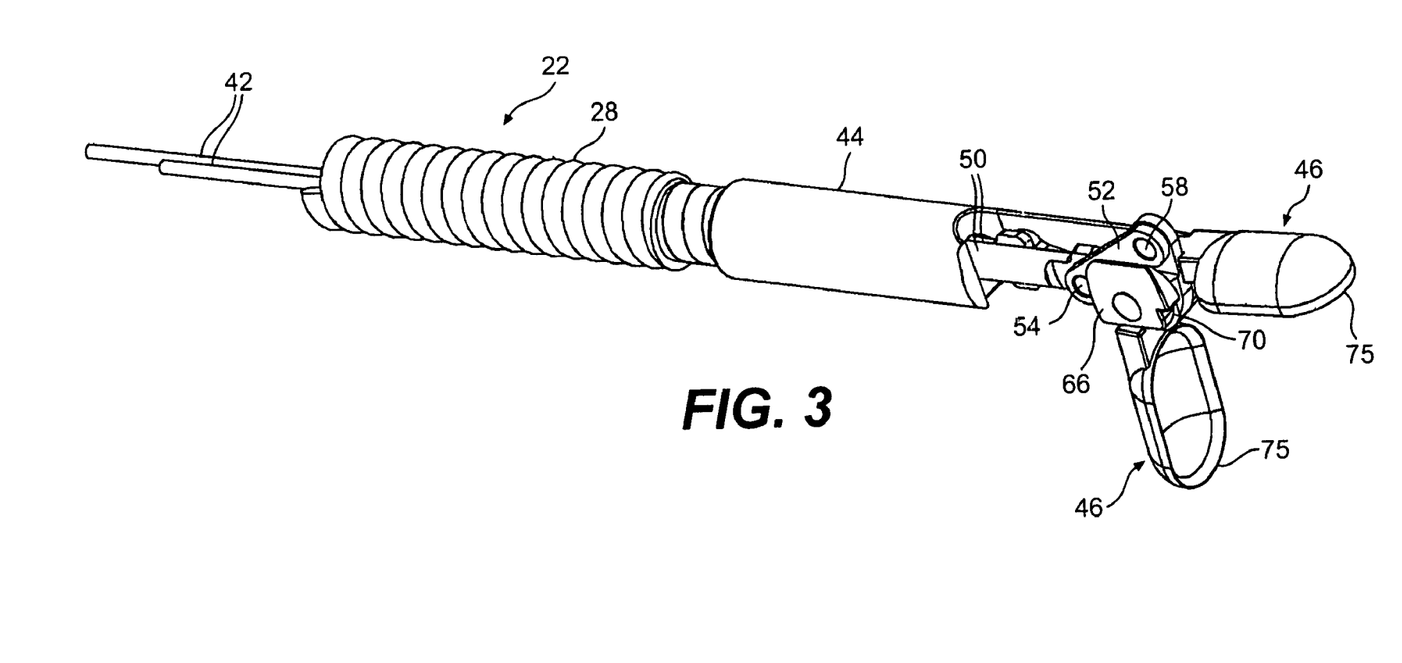
FIG. 3 is a perspective view of the distal end of the endoscopic medical instrument shown in FIG. 2 with the end effector assembly in a different orientation.

Tubular member 22 should be made of a material that has sufficient stiffness, elasticity, and maneuverability to sustain, for example, bending and shear forces incurred during an endoscopic operation. As best seen in FIGS. 2 and 3, the tubular member 22 may be made of a helical coil 28 covered with an outer sheath 30 (shown in FIG. 1). Tubular member 22 may be any suitable tubular member, such as, for example, a hollow, coil-less structure, and may be made of any suitable biocompatible materials known in the art.

As shown in FIG. 1, a handle 32 is attached to the proximal end of tubular member 22. Handle 32 is used to control or actuate a biopsy forceps assembly 34 within a body cavity. The handle 32 may be a conventional spool and shaft actuator having a spool 36 surrounding a shaft 38 that includes a thumb ring 40. A pair of flexible pull wires 42 of substantially equal length are attached to spool 36 in a manner well known in the art. The pull wires 42 are made out of steel or any other suitable material. A typical spool and shaft actuator is described in detail in U.S. Pat. No. 5,133,727, which is incorporated herein by reference. Other types of handles known in the art can also be used in combination with the tubular member and actuation mechanism of this invention. The handle shown and described is exemplary only.

As shown in FIGS. 1-3, an end effector assembly, for example, biopsy forceps assembly 34 includes a clevis 44 and a pair of end effectors, for example, forceps jaws 46, each of which is a duplicate of the other, pivotally connected to the clevis 44 via a clevis pin 48. Each pull wire 42 partially extends into the clevis 44 and attaches to a proximal end of one of a pair of actuators 50. Each actuator 50 is connected, in turn, to a proximal end of a link 52 near the distal end of the actuator via a pin 54 extending from the actuator 50. A distal end of each link 52 is connected to a tang 56 of a forceps jaw 46 extending proximally therefrom. The tang 56 includes a pin 58 to support the distal end of the link 52. Each of the pins 54 and 58 could be replaced with other pin arrangements, such as, for example, pins extending from the links or pins extending through the actuators, links, or tangs, or any other suitable connection known in the art, without departing from the heart of the invention.

Figure 4:
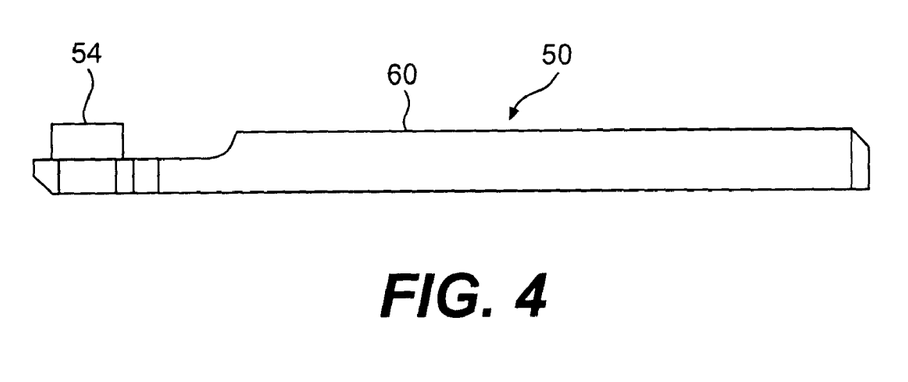
FIG. 4 is a plan view of the actuator of the instrument shown in FIG. 1.
Figure 5:
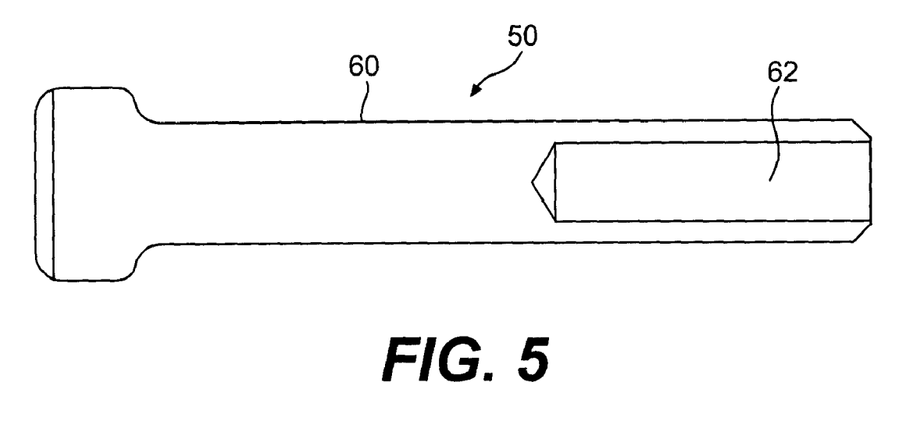
FIG. 5 is a side view of the actuator of the instrument shown in FIG. 1.
Figure 6:
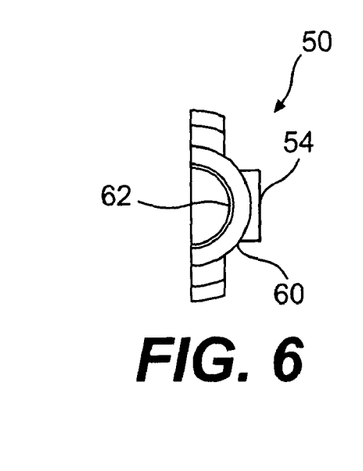
FIG. 6 is a proximal end view of the actuator of the instrument shown in FIG. 1.

As shown in FIGS. 4-6, each actuator 50 includes a main body portion 60 having a semi-circular cross-section and a recessed portion 62 formed in the flat inner surface of the semi-circular cross-section for attachment to one of the pull wires 42. The pin 54 extends from the outer surface of the actuator 50 opposite the flat surface of the semi-circular profile. In this configuration, both actuators 50 are free to move proximally and distally with respect to each other in the clevis 44 as the flat surface of one actuator 50 slides past the flat surface of the other actuator 50. Although an actuator 50 having a semi-circular cross-section has been shown in detail, the main body portion 60 may take many different shapes, such as, for example, tubular, rectangular, square, each with or without keying features. Examples of these profiles are shown in FIGS. 11A-11F and described below. Main body portions 60 of other cross-sections may be used.

Figure 7:
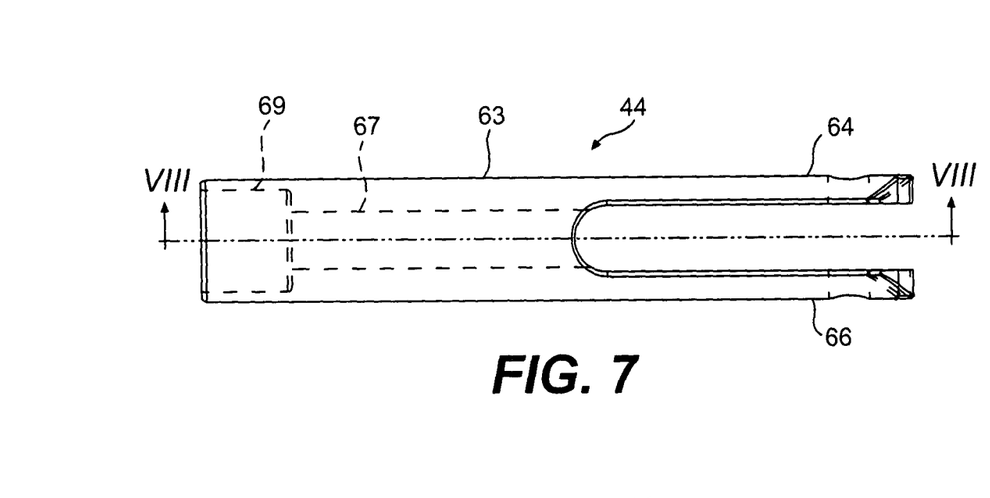
FIG. 7 is a plan view of the clevis of the instrument shown in FIG. 1.
Figure 8:
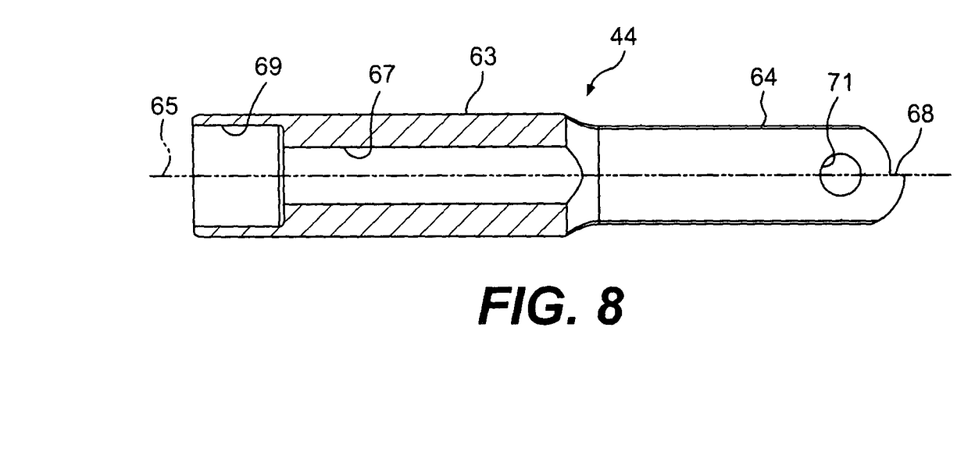
FIG. 8 is a cross-sectional view take along line VIII-VIII of FIG. 7.
Figure 9:
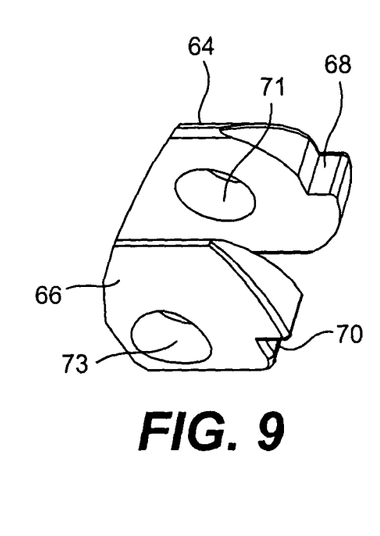
FIG. 9 is a perspective view of the distal portion of the clevis of FIG. 7.

FIGS. 7-9 show an embodiment of the clevis 44. Clevis 44 includes a cylindrical body portion 63 and a pair of clevis arms 64, 66 extending from the body portion 63 and configured to hold the clevis pin 48 in bores 71, 73. Each of the clevis arms 64, 66 includes a beveled surface leading to a stop 68, 70, respectively. These stops interact with stops on the jaws (as will be discussed below) to prevent over-rotation of the forceps jaws 46 beyond a center axis 65 of the clevis 44.

Figure 10:
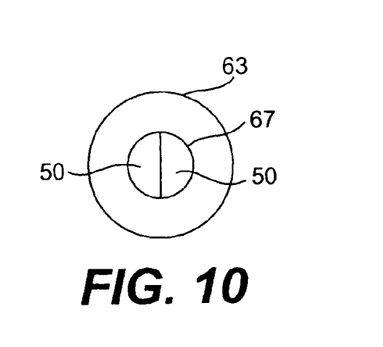
FIG. 10 is a schematic cross-sectional view of the clevis and actuators of the instrument taken along line X-X of FIG. 1.

Body portion 63 includes a through hole 67 sized to receive the proximal ends of both actuators 50 as shown in FIG. 10. In addition, as shown in FIG. 8, the proximal end of the clevis 44 includes a recessed portion 69 that is configured to affix the clevis to the tubular member 22 using any conventional means, such as, for example, crimping, swagging, gluing, laser welding, or otherwise adhering. Tubular member 22 may include a reduced diameter distal portion 22a received by recessed portion 69.

Figure 11A:
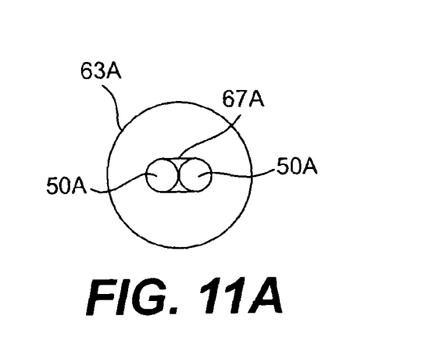
FIGS. 11A-F are schematic cross-sectional views of other exemplary embodiments of the clevis and actuator of the instrument shown in FIG. 1.
Figure 11B:
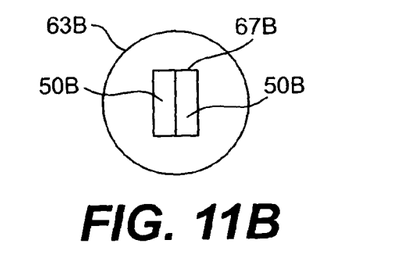
Figure 11C:
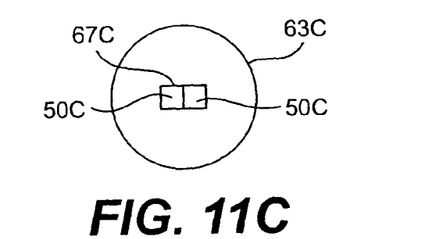
Figure 11D:
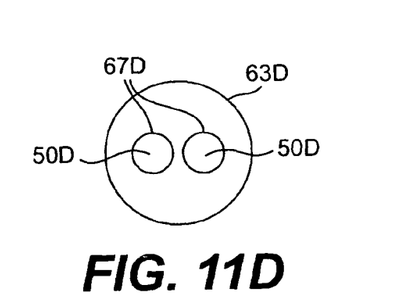
Figure 11E:
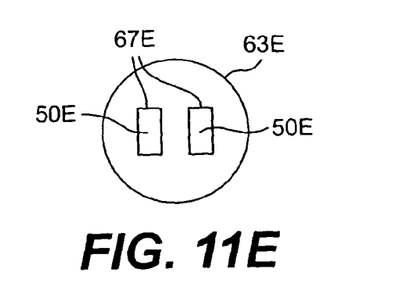
Figure 11F:
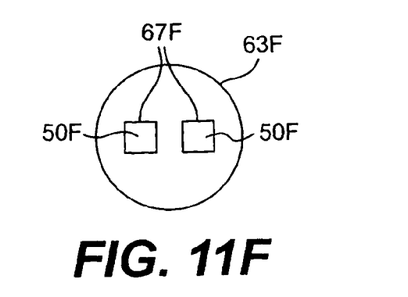

FIGS. 11A-11F show additional embodiments of devises having alternative through hole arrangements. These embodiments accommodate corresponding actuators of the same cross-sections. Actuators of differing cross-sections may be used. FIGS. 11A-11F show similar components to those shown in FIG. 10 and retain the same reference numerals with a letter matching the Figure number. In these Figures, the devises 63 include through holes 67 configured to receive actuators 50 having circular, rectangular, or square cross-sections. Other cross-sections may be used. The actuators also may include keying features. FIGS. 11A-11C show a single through hole, while FIGS. 11D-11F show two through holes. By varying the number of through holes and the cross-sections, different bearing surfaces can be provided to increase or decrease resistance to side loadings.

Referring back to FIGS. 1-3, the forceps jaws 46 are pivotally connected to clevis 44 such that they can be opened and closed to obtain a sample of tissue from within a body cavity. The forceps jaws 46 may be pivotally connected to the clevis 44 by a pin 48 that extends through both clevis arms 64, 66 or by any other suitable method known in the art, such as, for example, where the pin 48 extends from one of the clevis arms 64, 66 through the forceps jaws 46.

Figure 12:
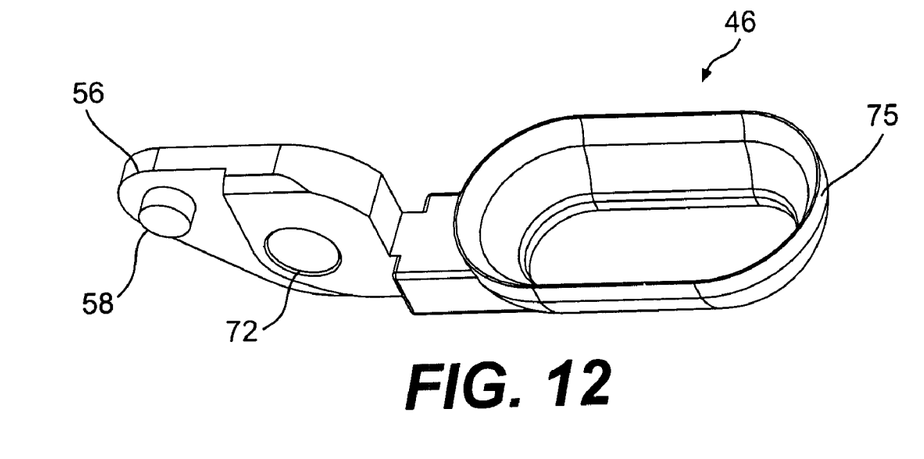
FIG. 12 is a perspective view of an end effector of the instrument shown in FIG. 1.
Figure 13:
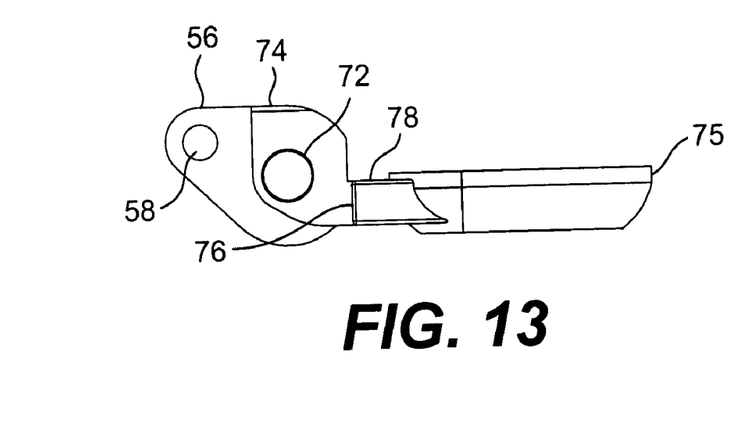
FIG. 13 is a side view of the end effector shown in FIG. 12.

FIGS. 12 and 13 show an exemplary embodiment of a forceps jaw 46 before being attached to the clevis 44. Because the lower and upper jaws of this embodiment are substantially identical, only one jaw 46 will be described. Forceps jaw 46, at its distal end, has a generally hemispherical shape with a cutting edge 75 located on a periphery. Alternatively, the cutting edge ring may be replaced with a plurality of teeth, if desired. A bore 72 is located within the tang portion 56 of jaw 46. The bore 72 is configured to receive the clevis pin 48 and to allow the forceps jaw 46 to pivot about the clevis pin 48. Jaw 46 also includes pin 58 that connects to the distal end of a link 52.

Three stop surfaces 74, 76, 78 are provided to assist in preventing over extension of the forceps jaw 46 during use. Specifically, when the forceps jaws 46 are assembled with other parts of the biopsy forceps device, the stop surface 74 of one forceps jaw 46 will contact with stop surface 76 of the other forceps jaw 46 to define the maximum opening angle, such as, for example, 100 degrees, between the two forceps jaws 46. This maximum open position is shown in FIGS. 2 and 3. Stop surfaces 74, 76 could be formed to define any other desired maximum opening angle. Stop surface 78 cooperates with one of the two stops 68, 70 of the clevis 44 to prevent the forceps jaws 46 from over-rotation past the center axis 65 of the clevis 44.

Having described all of the major components of the medical instrument 10, the use and operation of the instrument will now be described. To manipulate the opening and closing of the biopsy forceps assembly 34, the spool 36 is moved proximally and distally along the shaft 38. By moving the spool 36 distally, the pull wires 42 move distally causing the actuators 50 to move distally and to push on the proximal end of the links 52. This motion forces the forceps jaws 46 to open, as shown in FIG. 2.

FIG. 2 shows the forceps jaws 46 in a typical open configuration where the actuators 50 and the proximal ends of the links 52 have been displaced distally. By displacing the spool 36 proximally, the process is reversed and the forceps jaws 46 are closed and the cutting edges 75 can sever a biopsy sample from a tissue wall. The configuration of the actuation mechanism, including actuators 50 and links 52, permits the biopsy forceps jaws 46 to freely pivot about the clevis pin 48 while maintaining a strong closing force.

In FIG. 3, the pull wire 42, actuator 50, and link 52 associated with the open forceps jaw 46 is displaced distally with respect to the other pull wire 42, actuator 50, and link 52. To allow for such displacement, pull wire 42 may be configured to have some slack or to be pretensioned such that relative displacement of the link 52 and actuator 50 can be taken up by the pull wire 42 This allows one of the biopsy forceps jaws 46 to pivot about the clevis pin 48 independently of the other jaw 46, and thereby permits an operator, during an operation, to more accurately position the open jaws 46 to collect a biopsy sample. Such pretensioning or slack may cause the distance the spool travels to be much greater than is necessary to actuate the actuator 50 and cause the jaws 46 to open and close. The pretensioning or slack may be desirable, for example, to allow for the coiling of the device for packaging purposes or to allow for greater precision in actuating the actuator 50 and cause the jaws 46 to open and close.

During an operation, the distal end 24 of the elongate tube 22 and end effectors assembly 34 are inserted into a lumen of an endoscope and introduced into the body cavity of a patient. After reaching a target site where a medical procedure is to be performed on a portion of the body, such as, for example, obtaining a biopsy from a tissue wall, the spool 36 is displaced distally to open the end effectors 46. Next, the end effectors assembly 34 is moved into contact with the portion of the body. If the end effectors assembly 34 is not properly aligned, the distal portion 24 of the tubular member 22 may be manipulated so that the distal end of one end effector contacts the portion of the tissue wall proximal to the site from which a biopsy is desired. Alternatively, the distal end of the other end effector can contact the tissue wall opposing the site of interest. Then, the tubular member 22 may be further displaced distally, such as by pushing the entire device at the endoscope handle, thereby causing the end effector to bear on the tissue wall and rotate the end effector assembly 34 about the clevis pin 48 into position to act on the tissue wall. The slack or pretension in the pull wires 42 will allow this rotation. As shown in FIG. 3, the end effectors assembly 34 has rotated downward as if the lower end effector had contacted the tissue wall.

In the instance where the medical procedure to be performed is to obtain a biopsy, the cutting edge 75 of the lower biopsy jaw 46 contacts the tissue to be sampled. Further displacement of the tubular member 22 causes the end effectors assembly 34 to rotate (as shown in FIG. 3), thereby bringing the cutting edge 75 of the upper biopsy jaw 46 into contact with the tissue. The spool 36 then is displaced proximally to close the end effector assembly to complete the procedure. By displacing the spool 36 proximally, both actuators 50 will eventually move into alignment such that the end effectors will close substantially parallel to the center axis 65 of the clevis 44. This will occur because the slack will be taken up or the original pretension of the pull wire 46 will be restored. In some instances, the distal portion 24 of the tubular member 22 may bend upwards or downwards to allow the end effectors to close substantially parallel to the center axis 65. Similar results will occur if it is necessary to approach a tissue wall tangentially. The jaws 46 of the biopsy forceps assembly 34 will be able to rotate into the proper position to collect the sample once contact is made with the tissue wall. Although the above procedure has been described in relation to a fully open end effector assembly, it should be apparent that the end effector assembly can be pivoted with the end effector assembly at any degree of opening between zero degrees and the maximum opening so long as the pull wires have sufficient slack or pretension.

As described above, FIG. 3 shows one forceps jaws 46 in an open position while the other forceps jaw 46 is in a substantially closed position. The stop 68 on clevis arm 64 prevents the closed forceps jaw 46 from rotating past the center axis 65. Since the jaws are also limited in their relative rotation by stops 74, 78, preventing rotation of one jaw past the center axis limits the rotation of the open jaw 46 relative to the center axis to the maximum opening angle. This keeps the corresponding link 52 of the closed jaw 46 from rotating into alignment with the center axis 65. If such alignment were to occur (i.e. pull wire 42, actuator 50, link 52, pin 58, clevis pin 48 and center axis 65 are substantially in alignment), it would be difficult to close the forceps jaw 46 open or closed because there would be little or no torque available to cause the forceps jaw 46 to rotate about the clevis pin 48. The geometry of the forceps jaws 46 and the stops 68, 70 on clevis arms 64, 66 are configured to provide an angle greater than zero, for example, 15 degrees, between the center axis 65 of the clevis 44 and a longitudinal axis of the link 52 to avoid this problem.

In addition, this configuration of the links 52 and forceps jaws 46 ensures there will always be some closing force applied at the distal portion of the forceps jaws 46 during proximal displacement of the actuators 50. This is caused because there will always be a component of force from the proximal displacement of the spool acting perpendicular to a moment arm between the center of pin 58 and clevis pin 48, thereby providing a closing force on the distal end of the forceps jaws 46.

Figures 14, 15, 16, 17:
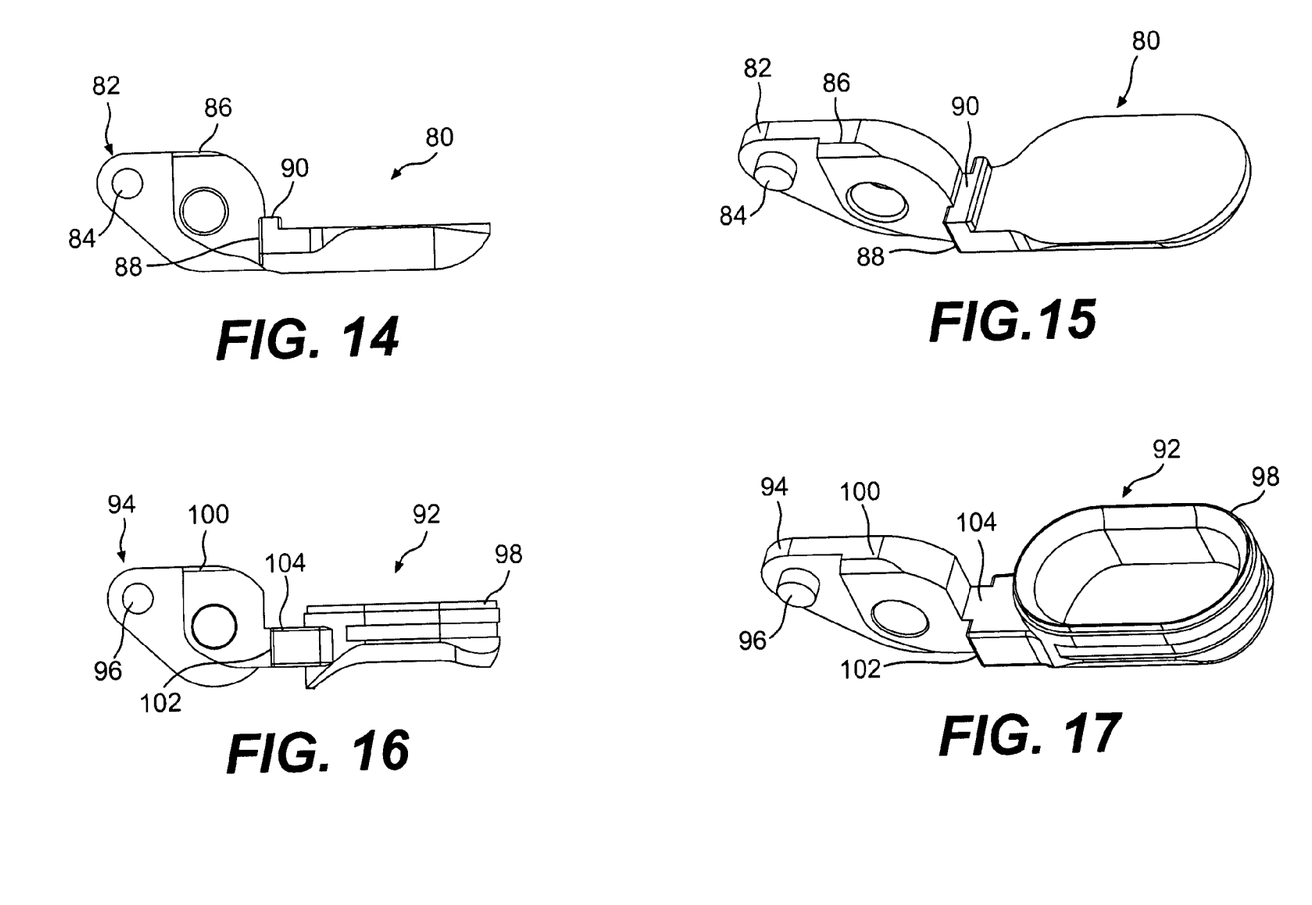
FIG. 14 is a side view of an upper end effector of another exemplary embodiment for use in the instrument shown in FIG. 1.
FIG. 15 is a perspective view of the end effector shown in FIG. 14.
FIG. 16 is a side view of a lower end effector of another exemplary embodiment for use in the instrument shown in FIG. 1.
FIG. 17 is a perspective view of the end effector shown in FIG. 16.

FIGS. 14-17 show an alternative embodiment of the forceps jaws 46 described above. FIGS. 14 and 15 show a forceps jaw assembly 80 that is configured similar to forceps jaw 46, with the exception that the forceps jaw 80 has a substantially planar distal portion as opposed to a substantially cup-shaped distal portion. Jaw 80 includes a tang portion 82, pin 84, and stop surfaces 86, 88, 90 that are structurally and functionally similar to those described for the forceps jaw 46.

FIGS. 16 and 17 show a forceps jaw assembly 92 for opposing jaw assembly 80. Assembly 92 is substantially similar to the forceps jaw 46. Jaw 92 includes a tang portion 94, pin 96, cutting edge 98, and stop surfaces 100, 102, 104 that are structurally and functionally similar to those described for the forceps jaw 46.

An endoscopic medical instrument having forceps jaws 80, 92 will operate substantially similarly to the operation described with respect to the instrument having forceps jaws 46. Because the forceps jaw 80 does not have a cutting edge, however, the biopsy sample is taken by pressing the cutting edge 98 of jaw 92 against the planar surface of forceps jaw 80. In all other aspects, this instrument may be used in the same manner as described above.

Figure 18:
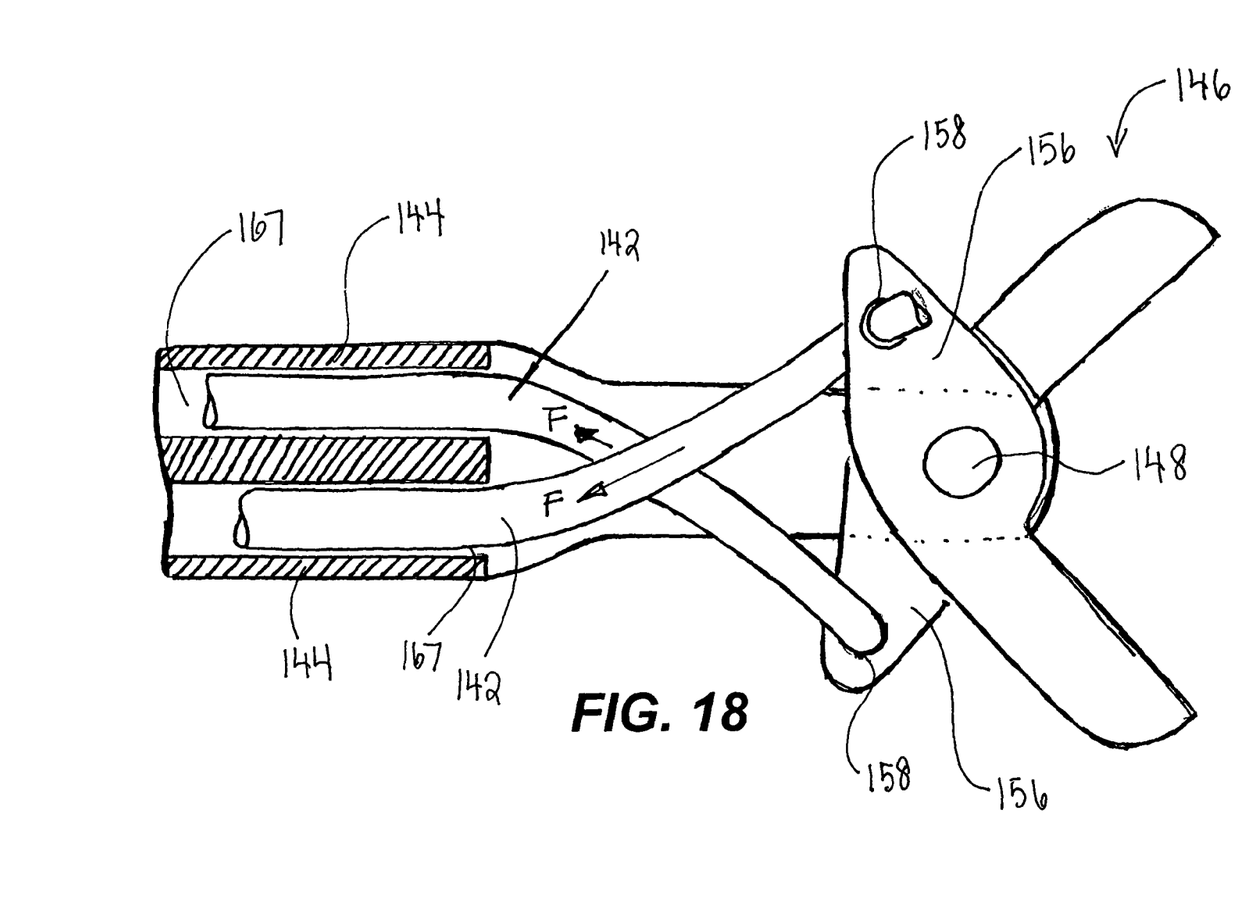
FIG. 18 is a schematic cross-sectional view of an another embodiment of a distal end of an endoscopic medical instrument of the present invention.

FIG. 18 shows an embodiment where the clevis 144 has two through holes 167 radially offset from a centerline of the endoscopic instrument. The pull wires 142 run through their respective through holes 167 and then cross once they exit the clevis 144. The pull wires 142 are each connected to one of the forceps jaws 146 at coupling portion 158 of tang portion 156. The forceps jaws 146 pivot about pin 148 on the clevis 144. By arranging the device in this manner, the angle at which the pull wire 142 acts on tang portion 156 when the pull wires 142 are moved proximally relative to the clevis 144 allows an increase in the closing force of the forceps jaws 146.

Figure 19:
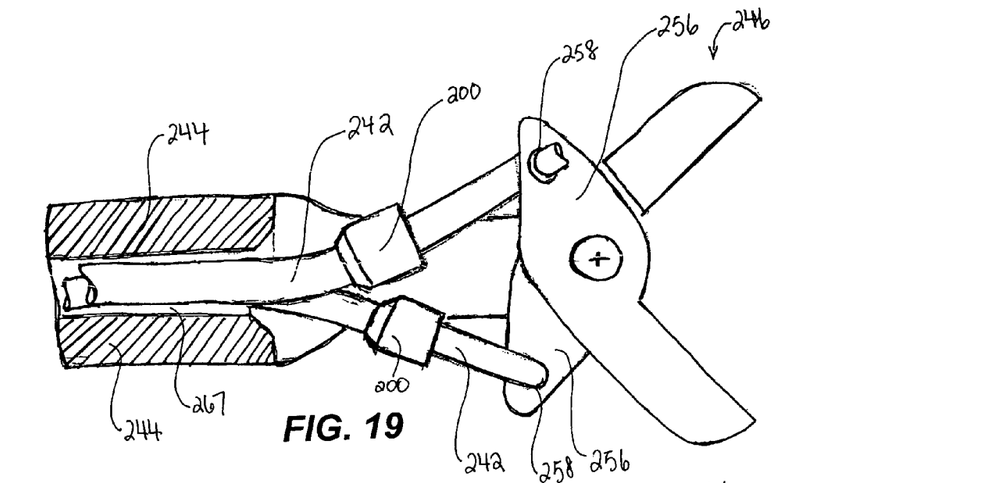
FIG. 19 is a schematic cross-sectional view of a further embodiment of a distal end of an endoscopic medical instrument of the present invention.
Figure 20:
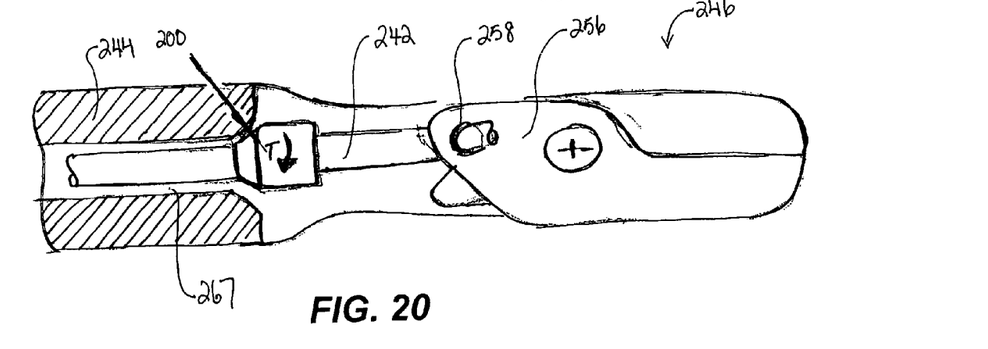
FIG. 20 is a schematic cross-sectional view of the distal end of the endoscopic medical instrument of FIG. 19.

FIGS. 19 and 20 show an embodiment where the pull wires 242 extend through the same hole 267 of the clevis 244 and are each connected to one of the forceps jaws 246 at coupling portion 258 of tang portion 256. The pull wires 242 each have a collar 200 fixed to it between the clevis 244 and the forceps jaw 246. When the pull wire 242 is moved proximally relative to the clevis 244, the chamfered end of the collar 200 comes into contact with a corresponding chamfered portion of the clevis 244. The contact causes the central axis of the collar 200 to become concentric with the central axis of the clevis 244, and in doing so causes an increase in the closing force of the forceps jaws 146.

Other embodiments of the invention will be apparent to those skilled in the art from consideration of the specification and practice of the invention disclosed herein. It is intended that the specification and illustrated examples are exemplary only, the true scope and spirit of the invention being apparent from the following claims.

What is claimed is:

1. A medical instrument, comprising:
    a tubular member having a distal end and a proximal end;
    a handle attached to the proximal end of the tubular member;
    a pair of end effectors supported on a pivot portion;
    an elongate member corresponding to each of the pair of end effectors, each elongate member extending through the tubular member and having a proximal end attached to the handle and a distal end coupled to the corresponding end effector, and
    a clevis attached to the distal end of the tubular member, wherein the clevis has a center axis and a pair of stops, each stop configured to prevent rotation of a corresponding end effector past the center axis, wherein the stops are formed in distalmost surfaces of the clevis,
    wherein each end effector includes a first stop surface and a second stop surface, wherein each of the first and second stop surfaces is proximal of a portion of the end effector defining a cutting edge, wherein the first stop surface of each of the pair of end effectors is a proximally facing wall, and
    wherein substantially the entire wall of the first stop surface of one of the end effectors contacts the second stop surface of the other of the end effectors at a maximum opening of the end effectors.

2. The medical instrument according to claim 1, wherein proximal displacement of the elongate member causes the corresponding end effector to close and distal displacement of the elongate member causes the corresponding end effector to open.

3. The medical instrument according to claim 1, wherein each elongate member is configured to move independently of the other elongate member.

4. The medical instrument according to claim 1, wherein the clevis supports a pivot pin supporting the end effectors.

5. The medical instrument according to claim 4, wherein each elongate member extends substantially parallel to the center axis.

6. The medical instrument according to claim 4, wherein portions of the pair of end effectors are disposed between portions of the clevis.

7. The medical instrument of claim 4, wherein the tubular member and the clevis are discrete components.

8. The medical instrument according to claim 1, wherein the clevis includes a main portion having at least one through hole configured to receive the elongate members.

9. The medical instrument according to claim 8, wherein the at least one through hole includes two through holes each configured to receive one of the elongate members.

10. The medical instrument according to claim 1, wherein each end effector is a forceps jaw.

11. The medical instrument according to claim 10, wherein one of the forceps jaws has a planar distal portion and the other of the forceps jaws has a cup-shaped distal portion.

12. The medical instrument according to claim 10, wherein at least one of the forceps jaws includes a cutting edge.

13. The medical instrument according to claim 1, wherein each elongate member is configured to move independent of the other elongate member to allow the end effectors to rotate about the pivot when the end effectors are at the maximum opening.

14. The medical instrument according to claim 1, wherein at least the distal end of one elongate member is displaceable a first amount proximally and at least the distal end of the other elongate member is displaceable a second amount distally to allow the end effectors to rotate about the pivot.

15. The medical instrument according to claim 14, wherein the first amount of displacement is different than the second amount of displacement.

16. The medical instrument of claim 1, further including a link corresponding to each of the pair of end effectors, and wherein a distal end of each link is connected to the corresponding end effector, and a proximal end of each link is connected to a distal end of the corresponding elongate member.

17. The medical instrument of claim 16, wherein each of the elongate members includes a flexible wire.

18. The medical instrument of claim 17, wherein each of the elongate members includes an actuator having a proximal end connected to a distal end of the corresponding flexible wire and a distal end connected to the corresponding link.

19. The medical instrument according to claim 18, wherein each actuator is more rigid than the corresponding flexible wire.

20. The medical instrument according to claim 19, wherein each actuator has a cross-section selected from one of semicircular, circular, rectangular, and square.

21. A medical instrument, comprising:
a tubular member having a distal end and a proximal end;
a handle attached to the proximal end of the tubular member;
a distal assembly including a pivot portion and an end effector assembly supported on the pivot portion, the end effector assembly having a pair of end effectors, the distal assembly having a center axis and a pair of stops, each stop configured to prevent rotation of a corresponding end effector past the center axis; and
an elongate member corresponding to each of the pair of end effectors, each elongate member extending through the tubular member and having a proximal end attached to the handle and a distal end attached to the end effector assembly in a manner permitting positioning of one of the end effectors at a first angle relative to the center axis when the other of the end effectors is positioned at a second angle relative to the center axis that is different than the first angle,
wherein the distal assembly further comprises a clevis attached to the distal end of the tubular member,
wherein the pair of stops are disposed distal to a throughhole of the clevis about which the pair of end effectors pivot, and
wherein the stops are formed in distalmost surfaces of the clevis.

22. The medical instrument according to claim 21, wherein each of the elongate members includes a flexible wire.

23. The medical instrument according to claim 22, wherein each of the elongate members includes an actuator having a proximal end connected to a distal end of the corresponding flexible wire and a distal end connected to the corresponding link.

24. The medical instrument according to claim 23, wherein each actuator is more rigid than the corresponding flexible wire.

25. The medical instrument according to claim 24, wherein each actuator has a cross-section selected from one of semicircular, circular, rectangular, and square.

26. The medical instrument according to claim 21, wherein proximal displacement of the elongate member causes the corresponding end effector to close and distal displacement of the elongate member causes the corresponding end effector to open.

27. The medical instrument according to claim 21, wherein each elongate member is configured to move independently of the other elongate member.

28. The medical instrument according to claim 21, wherein the clevis supports a pivot pin supporting the end effectors.

29. The medical instrument according to claim 28, wherein portions of the pair of end effectors are disposed between portions of the clevis.

30. The medical instrument according to claim 21, wherein each elongate member extends substantially parallel to the center axis.

31. The medical instrument according to claim 21, wherein the clevis includes a main portion having at least one through hole configured to receive the elongate members.

32. The medical instrument according to claim 31, wherein the at least one through hole includes two through holes each configured to receive one of the elongate members.

33. The medical instrument according to claim 21, wherein each end effector is a forceps jaw.

34. The medical instrument according to claim 33, wherein one of the forceps jaws has a planar distal portion and the other of the forceps jaws has a cup-shaped distal portion.

35. The medical instrument according to claim 33, wherein at least one of the forceps jaws includes a cutting edge.

36. The medical instrument according to claim 21, wherein each end effector includes a first stop surface and a second stop surface.

37. The medical instrument according to claim 36, wherein the first stop surface is a proximally facing wall, and wherein the substantially entire wall of the first stop surface of one of the end effectors contacts the second stop surface of the other of the end effectors at a maximum opening of the end effectors.

38. The medical instrument according to claim 37, wherein each elongate member is configured to move independent of the other elongate member to allow the end effectors to rotate about the pivot when the end effectors are at the maximum opening.

39. The medical instrument according to claim 21, wherein at least the distal end of one elongate member is displaceable a first amount proximally and at least the distal end of the other elongate member is displaceable a second amount distally to allow the end effectors to rotate about the pivot.

40. The medical instrument according to claim 39, wherein the first amount of displacement is different than the second amount of displacement to allow the corresponding end effectors to rotate through different angles about the pivot.

41. The medical instrument of claim 21, wherein the tubular member and the clevis are discrete components.

42. A medical instrument, comprising:
a tubular member having a distal end and a proximal end;
a handle attached to the proximal end of the tubular member;
a clevis coupled to the distal end of the tubular member so as to be stationary relative to the tubular member, the clevis defining first and second through holes extending through an interior of a body portion of the clevis, the first and second through holes each offset from and parallel to a centerline of the clevis;
a pair of end effectors supported on a pivot portion of the clevis;

a first elongate member corresponding to one of the pair of end effectors, extending through the tubular member and the first through hole, and having a proximal end attached to the handle; and a second elongate member corresponding to the other of the pair of end effectors, extending through the tubular member and the second through hole, and having a proximal end attached to the handle, wherein portions of the pair of end effectors are disposed between arms of the clevis, and wherein the clevis has a pair of stops formed in distalmost surfaces of the clevis and configured to prevent rotation of a corresponding end effector past the centerline.

43. The medical instrument of claim 42, wherein the arms are substantially parallel to each other.

44. The medical instrument of claim 42, wherein the arms are disposed radially outward from the portions of the pair of end effectors.

45. The medical instrument of claim 42, wherein the arms includes a pair of arms extending distally and defining a space therebetween for the pair of end effectors.

46. The medical instrument of claim 42, wherein the tubular member and the clevis are discrete components.

47. The medical instrument of claim 42, wherein a distal end of the first elongate member attaches to a proximal end of a first actuator, and a distal end of the second elongate member attaches to a proximal end of a second actuator.

* * * * *